(12) United States Patent
Bilat

(10) Patent No.: US 11,179,527 B2
(45) Date of Patent: Nov. 23, 2021

(54) CONTROL OF TOTAL PARTICULATE MATTER PRODUCTION

(71) Applicant: Altria Client Services LLC, Richmond, VA (US)

(72) Inventor: Stephane Bilat, Areuse (CH)

(73) Assignee: Altria Client Services LLC, Richmond, VA (US)

( * ) Notice: Subject to any disclaimer, the term of this patent is extended or adjusted under 35 U.S.C. 154(b) by 300 days.

(21) Appl. No.: 16/031,309

(22) Filed: Jul. 10, 2018

(65) Prior Publication Data

US 2019/0008209 A1   Jan. 10, 2019

Related U.S. Application Data

(63) Continuation of application No. PCT/EP2018/066699, filed on Jun. 22, 2018.

(30) Foreign Application Priority Data

Jul. 10, 2017   (EP) .................................... 17180611

(51) Int. Cl.
*A61M 15/06* (2006.01)
*A61M 11/04* (2006.01)
(Continued)

(52) U.S. Cl.
CPC ............. *A61M 15/06* (2013.01); *A24F 40/51* (2020.01); *A24F 40/65* (2020.01); *A61M 11/001* (2014.02);
(Continued)

(58) Field of Classification Search
CPC ....... A61M 11/001; A24F 40/50; A24F 40/51; A24F 40/53
See application file for complete search history.

(56) References Cited

U.S. PATENT DOCUMENTS 8,820,330 B2    9/2014  Bellinger et al.
2014/0321837 A1*  10/2014  Flick ..................... F24H 9/2014
                                                  392/387
(Continued)

FOREIGN PATENT DOCUMENTS

WO   WO-2013/060781 A1   5/2013
WO   WO-2013/098398 A2   7/2013
(Continued)

OTHER PUBLICATIONS

International Search Report and Written Opinion for correspondng PCT Application No. PCT/EP2018/066699 dated Jul. 12, 2018.
(Continued)

*Primary Examiner* — Erin E McGrath
(74) *Attorney, Agent, or Firm* — Harness, Dickey & Pierce, P.L.C.

(57) ABSTRACT

Systems, devices, and methods may control total particulate matter (TPM) production based on air flow rate and TPM density. TPM density is a TPM production rate per flow rate of gas through an aerosol-generating device. The systems, devices, and methods may measure, or sample, air flow
(Continued)

during a puff or draw on an aerosol-generating device. The aerosol-generating device may, in turn, adjust the production of the TPM based on the measured air flow rate and a selected, or desired, TPM density, which may be pre-set in the device and/or subsequently set as desired.

11 Claims, 10 Drawing Sheets

(51) Int. Cl.
*A61M 11/00* (2006.01)
*A24F 40/51* (2020.01)
*A24F 40/65* (2020.01)
*A61M 16/00* (2006.01)
*A24F 40/10* (2020.01)

(52) U.S. Cl.
CPC ............ *A61M 11/042* (2014.02); *A24F 40/10* (2020.01); *A61M 2016/0027* (2013.01); *A61M 2016/0039* (2013.01); *A61M 2205/3334* (2013.01); *A61M 2205/3569* (2013.01); *A61M 2205/3592* (2013.01); *A61M 2205/3653* (2013.01); *A61M 2205/502* (2013.01); *A61M 2205/52* (2013.01); *A61M 2205/8206* (2013.01)

(56) References Cited

U.S. PATENT DOCUMENTS

| 2016/0157524 A1* | 6/2016 | Bowen .............. A61M 15/0065 128/200.14 |
| 2016/0278435 A1 | 9/2016 | Choukroun et al. |
| 2017/0119058 A1 | 5/2017 | Cameron |

FOREIGN PATENT DOCUMENTS

| WO | WO-2015/189556 A1 | 12/2015 |
| WO | WO-2016/029225 A1 | 2/2016 |
| WO | WO-2016/090303 A1 | 6/2016 |
| WO | WO-2016/096482 A1 | 6/2016 |

OTHER PUBLICATIONS

European Search Report for European Serial No. 17180611 dated Mar. 21, 2018.

* cited by examiner

Fig. 5

| Level | TPM Density (mg/s/ml/s) | Air Flow Speed (ml/s) | Power | TPM Per Second (mg/s) | TPM for 3 Second Puff (mg) |
|---|---|---|---|---|---|
| 1 | 0.05 | 10 | Power defined for 10 ml/s | 0.5 | 1.5 |
|   |      | 20 | Power defined for 20 ml/s | 1 | 3 |
|   |      | 30 | Power defined for 30 ml/s | 1.5 | 4.5 |
| 2 | 0.075 | 10 | Power defined for 10 ml/s | 0.75 | 2.25 |
|   |       | 20 | Power defined for 20 ml/s | 1.5 | 4.5 |
|   |       | 30 | Power defined for 30 ml/s | 2.25 | 6.75 |
| 3 | 0.1 | 10 | Power defined for 10 ml/s | 1 | 3 |
|   |     | 20 | Power defined for 20 ml/s | 2 | 6 |
|   |     | 30 | Power defined for 30 ml/s | 3 | 9 |

Fig. 6

| Air Level Range (ml/s-ml/s) | Power (Watts) |
|---|---|
| 0-10 | 3 |
| 10-20 | 3.5 |
| 20-30 | 4.2 |
| 30-40 | 5.1 |
| 40-50 | 6.5 |

Fig. 7

| Sample | Air Flow (ml/s) | Air Level Range (ml/s-ml/s) | Power (Watts) |
|---|---|---|---|
| S0 | 8 | 0-10 | 3 |
| S1 | 16 | 10-20 | 3.5 |
| S2 | 23 | 20-30 | 4.2 |
| S3 | 33 | 30-40 | 5.1 |
| S4 | 37 | 30-40 | 5.1 |
| S5 | 41 | 40-50 | 6.5 |
| S6 | 41 | 40-50 | 6.5 |
| S7 | 41 | 40-50 | 6.5 |
| S8 | 33 | 30-40 | 5.1 |
| S9 | 24 | 20-30 | 4.2 |
| S10 | 13 | 10-20 | 3.5 |

CONTROL OF TOTAL PARTICULATE MATTER PRODUCTION

CROSS-REFERENCE TO RELATED APPLICATIONS

This is a continuation of and claims priority to PCT/EP2018/066699, filed on Jun. 22, 2018, and further claims priority to EP 17180611.0, filed on Jul. 10, 2017, both of which are hereby incorporated by reference in their entirety.

BACKGROUND

Field

Example embodiments relate to systems, devices, and methods for use in controlling vapor generation from pre-vapor formulations or total particulate matter production in aerosol generation from aerosol-producing substrates in view of a total particulate matter density. The devices herein may be referred to as e-vapor devices or aerosol-generating devices.

Description of Related Art

When a higher level of total particulate matter (TPM) (including, for example, propylene glycol, glycerin, nicotine, water particles, etc.) is desired, an inhalation, or puff, may be performed to generate a higher flow rate. In other words, the inhalation, or puff, may need to be stronger or harder to receive a higher level of TPM.

In various aerosol-generating devices, such as those that generate aerosol by the transfer of heat from a heat source to a physically-separate aerosol-producing substrate that includes, for example, a substrate-containing tobacco, stronger inhalations, or puffs, to generate a higher flow rate may not necessarily increase the rate of TPM generation, or production, by the aerosol-generating devices. For example, in some aerosol-generating devices, a stronger puff in terms of flow rate may generate more cooling of the heat source, or heater, of the aerosol-generating devices, which in turn, may generate less TPM during the puff in terms of mass of TPM per volume per second.

Thus, while cigarettes may increase TPM generation in response to an inhalation having a higher flow, aerosol-generating devices may not increase TPM generation and may actually decrease TPM generation in response to an inhalation having a higher flow. In other words, the TPM generated, or produced, by the aerosol-generating devices is often the same or similar regardless of the rate of inhalation. For example, a larger flow rate within an aerosol-generating device often results in a decrease in production of TPM due to the larger flow rate cooling the heating element configured to generate aerosol from an aerosol-producing substrate in response to the heat, which may be contrary to a desired or expected outcome.

Therefore, such aerosol-generating devices may provide a less desirable experience because inhalations, or puffs, having a higher flow rate may not match the expected TPM generation. Furthermore, expectations when switching to reduced-risk aerosol-generating devices may be impeded, because reduced-risk aerosol-generating devices may not provide the same experience with respect to TPM generation.

A number of aerosol-generating devices may adjust one or more parameters related to the production of aerosol for various reasons but none of such devices appear to adjust such parameters to maintain TPM generation at a particular level with respect to flow rate.

SUMMARY

A method of controlling a production of a total particulate matter (TPM) in an aerosol-generating device may include determining a flow rate of a gas through the aerosol-generating device. The method may additionally include adjusting the production of the total particulate matter (TPM) by the aerosol-generating device in response to the flow rate and a TPM density as a target. The TPM density is a TPM production rate per flow rate of the gas through the aerosol-generating device.

An aerosol-generating device may include an aerosol-generating element, a flow sensor, a power source, and a controller. The aerosol-generating element may be configured to heat an aerosol-producing substrate for a production of a total particulate matter (TPM). The flow sensor may be configured to measure a flow rate of a gas to the aerosol-generating element. The power source may be configured to provide power to the aerosol-generating element. The controller may include one or more processors and be operably coupled to the power source, the flow sensor, and the aerosol-generating element. The controller may be configured to adjust the production of the TPM in response to the flow rate and a TPM density as a target. The TPM density is a TPM production rate per flow rate of the gas.

A user interface device may include a communication interface, a display, and a controller. The communication interface may be configured to communicate with an aerosol-generating device. The display may include a graphical user interface configured to present options for a TPM density. The controller may include one or more processors and be operably coupled to the display and the communication interface. The controller may be configured to display the options for the TPM density on the graphical user interface, to allow a selection of the TPM density, and to communicate the selection of the TPM density to the aerosol-generating device.

A non-transitory computer readable storage medium may include a computer program stored thereon which, when run on programmable electric circuitry, causes the programmable electric circuitry to determine a flow rate of a gas through an aerosol-generating device and to adjust a production of a total particulate matter (TPM) by the aerosol-generating device in response to the flow rate and a TPM density as a target. The TPM density is a TPM production rate per flow rate of the gas through the aerosol-generating device.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 5 is a table of TPM density and the air flow rates that affect TPM production according to an example embodiment.

FIG. 6 is a look-up table of power values for various air flow levels usable to determine the power to generate a desired TPM density according to an example embodiment.

FIG. 7 is a table depicting an air flow and power level over time according to an example embodiment.

DETAILED DESCRIPTION

Figure 1:
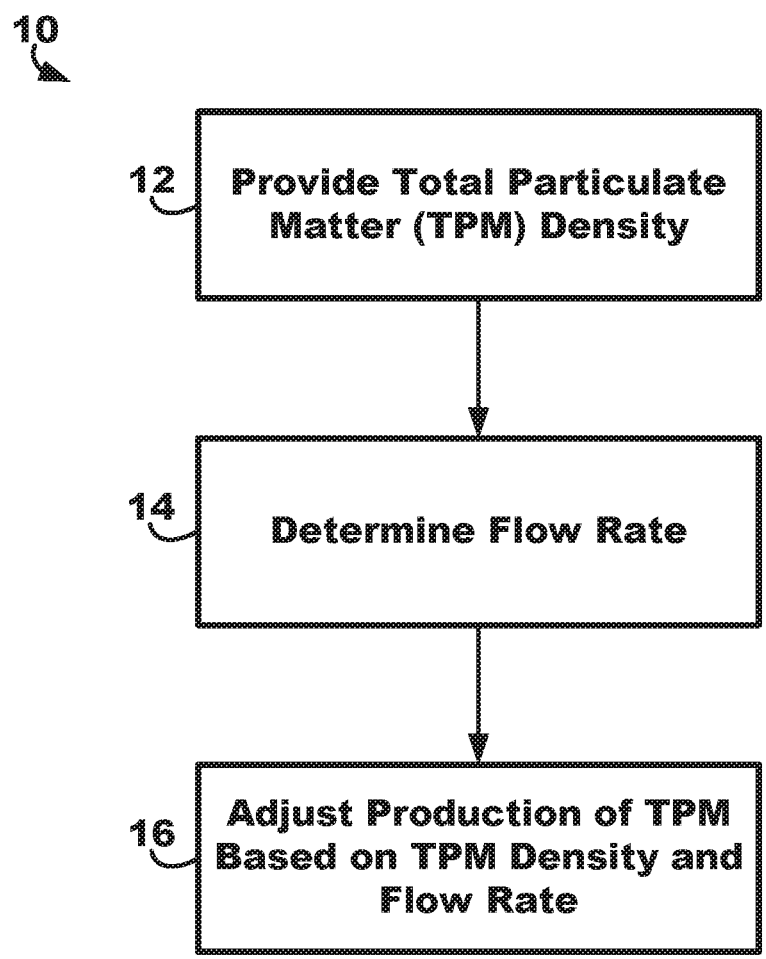
FIG. 1 is a flow chart of a method of controlling a production of total particulate matter (TPM) in an aerosol-generating device according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Some example embodiments provide increased levels of TPM in response to inhalations, or puffs, having increased flow rates. For example, when a higher flow rate is sensed or determined, the TPM production may be increased to correspond to the higher flow rate. Conversely, for example, when a lower flow rate is sensed or determined, the TPM production may be decreased to correspond to the lower flow rate. As a result, the strength of a puff may be adjusted in an instinctive manner to provide a desired level of TPM.

Some example embodiments regulate TPM production in view of maintaining the desired TPM density.

Some example embodiments allow a selection of the desired level TPM density, for example, using the aerosol-generating device or a user interface device.

In various aspects, methods of and devices and systems are for controlling total particulate matter (TPM) production in an aerosol-generating device using an aerosol-producing substrate. The method may include providing a TPM density where the TPM density is a TPM production rate (such as milligrams per second) per flow rate of gas through the aerosol-generating device (such as millilitres per second), determining a flow rate of gas through the aerosol-generating device, and adjusting production of TPM by the aerosol-generating device in response to the determined flow rate to maintain the TPM density. Further, a selection of the desired TPM density may be made using an aerosol-generating device or a user interface device. More specifically, in various aspects, systems, devices, and methods are configured to determine a flow rate of gas through the aerosol-generating device and adjust production of TPM by the aerosol-generating device in response to the determined flow rate and a desired TPM density to target the desired TPM density.

In various aspects, aerosol-generating devices may include an aerosol-generating element comprising at least one heating element to heat an aerosol-producing substrate to generate aerosol to flow through a channel, a flow sensor to measure the flow rate of gas through the channel, a power source operably coupled to the aerosol-generating element to provide power to the aerosol-generating element, and a controller comprising one or more processors and operably coupled to the power source, the flow sensor, and the aerosol-generating element. The controller may be configured to execute the one or more processes for controlling TPM production in view of air flow and TPM density. In other words, it may be described that a combination of hardware and software may be used to increase the power delivered to the heater of an aerosol-generating device as a function of the sensed increased air flow. In at least one illustrative embodiment, the aerosol-generating device may be configured for the aerosol generation to be a constant ratio corresponding to the amount of TPM per air flow volume per second.

In various aspects, a selection of a desired TPM density level may be made, for example, using the aerosol-generating device or a user interface device. The user interface device may include a communication interface to communicate with an aerosol-generating device, a display comprising a user interface to present a desired TPM density selection region, and a controller comprising one or more processors and operably coupled to the display and the communication interface. The controller of the user interface device may be configured to display a desired TPM density selection region on the user interface, to allow a selection of a desired TPM density, and to communicate the selected desired TPM density to the aerosol-generating device.

Various aspects of the systems, devices, and methods may provide one or more advantages relative to currently available aerosol-generating articles and associated systems. The systems, devices, and methods may provide a more desirable experience, since aerosol production is related directly to each inhalation and the expectations associated with such inhalation. For example, during a relatively quick inhalation, the experience will include the expected result of an increased level of TPM production. Furthermore, for example, a satisfying result may be obtained with an inhalation having a reasonable length as opposed to an inhalation having an extended duration to generate the same or similar amount of TPM. Additionally, the aerosol-generating device may be customized or configured to deliver a desired TPM density by making the appropriate selection on the aerosol-generating device or a user interface device.

As used herein, "aerosol-producing substrate" is any substrate capable of releasing, upon heating, volatile compounds, which can form an aerosol. The aerosols generated from aerosol-producing substrates according to the present disclosure may be visible or invisible and may include vapours (for example, fine particles of substances, which are in a gaseous state, that are ordinarily liquid or solid at room temperature) as well as gases and liquid droplets of condensed vapours.

As used herein, "aerosol-generating device" is any device configured to use, or utilize, an aerosol-producing substrate that releases volatile compounds to form an aerosol.

As used herein, "TPM density" is a TPM production rate (such as milligrams per second) per flow rate of gas through the aerosol-generating device (such as millilitres per second).

As used herein, "flow sensor" is any device or apparatus capable of measuring, or sensing, air flow or air flow rate through the aerosol-generating device. The flow sensor may include any electromechanical devices, mechanical devices, optical devices, micro-electrical mechanical systems (MEMS), MEMS pressure sensors, capacitive sensors, acoustic sensors, thermal conductive sensors, pressure sensors, mass airflow sensors, anemometers, or any combination thereof.

Example embodiments relate to aerosol-generating devices that are configured to use aerosol-producing substrates to generate aerosol containing particulate matter such as nicotine. The particulate matter may be measured using total particulate matter (TPM) such as, for example, the total mass of particulate matter for a selected volume.

The aerosol-generating device may define a cavity for receiving an aerosol-producing substrate (one or more of, for example, a liquid, a solid, and gas) and may include a heater configured to heat the aerosol-producing substrate to generate aerosol. The aerosol-generating device may include a power supply to at least power the heater and may be configured to be interfaced, or operatively coupled, to a host device. The host device may include an interface to be interfaced, or operably coupled, to the aerosol-generating device to at least charge the power supply of the aerosol-generating device.

The aerosol-generating device may further include a flow sensor to detect a flow rate of air through the aerosol-generating device, or more specifically, through one or more of a mouth piece, a cavity, and an inlet opening into the cavity. The flow rate may be used to adjust the production of TPM in view of a selected, or desired, TPM density as described herein.

The aerosol-generating device may include a controller comprising one or more processors (for example, microprocessors) and a communication interface (for example, wireless communication interface such as a BLUETOOTH wireless protocol interface) to transfer data to and from a user interface device. The one or more processors may operate with associated data storage, or memory, for access to processing programs or routines and one or more types of data that may be employed to carry out the illustrative methods. For example, processing programs or routines stored in data storage may include programs or routines for flow rate calculations, TPM productions calculations, temperature calculations, TPM density calculations, power calculations for producing TPM using particular aerosol-producing substrates and various aerosol-generating elements, performing statistics (for example, averages, medians, modes, etc.), matrix mathematics, standardization algorithms, comparison algorithms, or any other processing used to implement the one or more illustrative methods and processes described herein. Further, for example, processing programs or routines stored in data storage may include processes and functions to wirelessly transfer data and commands between one or more of the aerosol-generating device, a user interface device, and remote devices or servers. The data storage, or memory, may be further configured to store data related one or more types of aerosol-producing substrates, one or more types of aerosol-generating devices, TPM densities related to the one or more types of aerosol-producing substrates and devices, power values and formulas for various TPM densities and aerosol-producing substrates, data and formulas related to the generation of particulate matter using the aerosol-generating device, and any other data or formulas necessary to perform the processes and methods described herein. The aerosol-generating device may be configured to communicate, for example, using the communication interface, with the user interface device to transmit data representative of a selected TPM density or values associated therewith.

In one or more embodiments, the aerosol-generating device may be described as being implemented using one or more computer programs executed on one or more programmable processors that include processing capabilities (for example, microcontrollers, programmable logic devices, etc.), data storage (for example, volatile or non-volatile memory or storage elements), input devices, and output devices. Program code, or logic, described herein may be applied to input data to perform functionality described herein and generate desired output information. The output information may be applied as input to one or more other devices or processes as described herein or as would be applied in a known fashion.

The computer program products used to implement the processes described herein may be provided using any programmable language, for example, a high-level procedural or object orientated programming language that is suitable for communicating with a computer system. Any such program products may, for example, be stored on any suitable device, for example, a storage media, readable by a general or special purpose program, controller apparatus for configuring and operating the computer when the suitable device is read for performing the procedures described herein. In other words, at least in one embodiment, the user interface device may be implemented using a non-transitory computer readable storage medium, configured with a computer program, where the storage medium so configured causes the computer to operate in a specific and predefined manner to perform functions described herein.

The exact configuration of the controller of the aerosol-generating device is not limiting and essentially any device capable of providing suitable computing capabilities and control capabilities to implement the illustrative methods described herein may be used. In view of the above, it will be readily apparent that the functionality as described in one or more example embodiments may be implemented in any manner as would be known to one skilled in the art. As such, the computer language, the controller, or any other software/hardware which is to be used to implement the processes described herein shall not be limiting on the scope of the systems, processes, or programs (for example, the functionality provided by such processes or programs) described herein. The methods and processes described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, CPLDs, microcontrollers, or any other equivalent integrated or discrete logic circuitry, as well as any combinations of such components. When implemented in software, the functionality ascribed to the systems, devices, and methods described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality.

An illustrative method of controlling TPM production may include providing a TPM density. The TPM density can be provided in a variety of ways. The TPM density may be input into the aerosol-generating device directly or indirectly using another device such as, for example, a user input device. The TPM density may also be preset by the aerosol-generating device, which may be adjusted at a later time. Furthermore, the TPM density preset may be adjusted by the manufacturer through, for example, a software update over a network or the like.

The numerical TPM density may not be presented for selection. Instead, TPM levels that correspond to various TPM densities may be presented for selection. For example, a high TPM level, a medium TPM level, and a low TPM level may be presented for selection. Alternatively, the selection of a TPM level may be presented within, or along, a numerical scale from 1 to 10, with 1 corresponding to the lowest TPM density and 10 level corresponding to the highest TPM density.

The illustrative method may determine a flow rate through the aerosol-generating device, for example, using a flow sensor. The flow rate may be measured, or sampled, periodically such as, for example, every $\frac{1}{10}$ second, every $\frac{1}{4}$ second, every $\frac{1}{2}$ second, every second, etc. In view of the measured flow rate, the TPM production may be adjusted in an effort to target the desired TPM density. TPM production may be adjusted in view of the flow rate to maintain the TPM density within a range of the desired TPM density. In other words, the TPM production may be controlled to keep the TPM density within a selected amount of the desired TPM density.

Further, the TPM production may be controlled, or adjusted, by modifying the amount of power delivered by an aerosol-generating element, or heater, of the aerosol-generating device to the aerosol-producing substrate. Generally, an increase in power delivered to the aerosol-generating element, or heater, will result in an increase in TPM production for a given flow rate. The power to the aerosol-generating element may be increased in response to, or initiated by, an increase in flow rate, and conversely, power to the aerosol-generating element may be decreased in response to, or initiated by, a decrease in flow rate. In one or more embodiments, the flow rate may be compared to various flow rate thresholds associated with different power levels to be applied the aerosol-generating element. Thus, the amount of power to be used to generate aerosol from the aerosol-producing substrate increases in response to the determined flow rate being greater than or equal to a flow rate threshold. Further, in at least one illustrative example, it may be described that the TPM production is proportional to the flow rate.

The amount of power to be delivered to the aerosol-generating element for particular flow rates and particular TPM densities may be stored in a memory of, for example, the aerosol-generating device, or alternatively, of the user interface device or in a remote server to be downloaded into one or more of the aerosol-generating device and the user interface device. In at least one illustrative embodiment, the amount of power to be delivered to the aerosol-generating element for particular flow rates and particular TPM densities may be stored in a table in memory. In at least one illustrative embodiment, the amount of power to be delivered to the aerosol-generating element, or heater, for particular flow rates and particular TPM densities may be defined by an equation or formula that may receive a flow rate and a TPM density as inputs and output a power value to be applied to the aerosol-generating element. In one illustrative embodiment, one or more TPM densities may be stored in memory for each of a plurality of different types of aerosol-producing substrates.

The illustrative systems, devices, and methods described herein may further include providing the type of aerosol-producing substrate to be or being used by the aerosol-generating device. The aerosol-generating device may be able to, or be configured to, detect the type of aerosol-producing substrate. In other illustrative embodiments, the type of aerosol-producing substrate may be input using the aerosol-generating device or a user interface device. Further, the power to be provided to the aerosol-generating element based on air flow rate and TPM density may be adjusted based on the type of aerosol-producing substrate, and thus may be described as being dependent on the type of aerosol-producing substrate.

As noted, example embodiments may include a user interface device. The user interface device may be a cellular telephone. In another embodiment, the user interface device is a smart watch. Generally, the user interface device may be described as any electronic device including a display for providing a graphical user interface. The user interface device includes a communication interface such as, for example, at least a telemetry circuit and an antenna, for bidirectional communication with other devices such as aerosol-generating devices, servers, network devices, personal computers, and the like and with other networks such as the internet and the like. More specifically, data and commands may be transmitted and received during uplink or downlink telemetry between the user interface device and other devices or networks using the communication interface. In at least one embodiment, the communication interface is a wireless interface using one or more wireless (for example, radio frequency) data transmission protocols such as, for example, BLUETOOTH, WI-FI, any protocol in the ultra-high frequency (UHF) band, any protocol in the super high frequency (SHF) band, low frequencies, etc. The controller and communication interface of the user interface device may be similar to that the aerosol-generating device of described herein. In other words, the electronic intelligence may part of one or both of the user interface device and the aerosol-generating device.

The user interface device may further include a display operatively coupled to the controller for the output of data via the display. The display may be further configured to depict and be used as an interactable, graphical user interface. The graphical user interface and display may comprise a touchscreen. The graphical user interface may be described as being interactable because the graphical user interface may be configured to allow a viewing and/or manipulating of the data on the display, to allow an interaction with user interface device, to allow an interaction with the aerosol-generating device, and the like.

For example, the graphical user interface may be configured to display a TPM density dialog to facilitate a selection of a TPM density or at least a value related thereto such as a TPM level. The graphical user interface may allow a selection of a TPM density level such as, for example, low, medium, or high, which corresponds to numerical TPM densities for use in TPM production such as power values for various flow rates. In at least one aspect, the graphical user interface may display a question, or prompt, to input a desired TPM density such as, for example, "Please select a TPM density." Once the desired TPM density or value related thereto is selected, it may be transmitted to the aerosol-generating device to, for example, attempt to maintain the TPM density selected across a variety of flow rates.

Once the TPM density is selected using the graphical user interface, the TPM density or values related thereto may be transferred (for example, using the communication interfaces described herein) to the aerosol-generating device such that the aerosol-generating device may utilize the selected TPM density. Upon reception of the TPM density or values related thereto, the aerosol-generating device may be configured to control the production of TPM in view of the selected TPM density.

As used herein, "controller" and "processor" are any device or apparatus capable of providing suitable computing capabilities and control capabilities such as, for example, microprocessors, digital signal processors (DSP), application specific integrated circuits (ASIC), field-programmable gate arrays (FPGA), equivalent discrete or integrated logic circuitry, or any combination thereof and of providing suitable data storage capabilities that includes any medium (for example, volatile or non-volatile memory, a CD-ROM, magnetic recordable medium such as a disk or tape, etc.) containing digital bits (for example, encoded in binary, trinary, etc.) that may be one or more of readable and writeable.

As used herein, a "communication interface" is any device or apparatus capable of providing suitable data communication capabilities between an aerosol-generating device and a user interface device such as, for example, various telemetry circuits and antennas and may use one or more wired or wireless (for example, radio frequency) data transmission protocols such as, for example, BLUETOOTH, WI-FI, any protocol in the ultra-high frequency (UHF) band, any protocol in the super high frequency (SHF) band, low frequencies, or combinations thereof.

As used herein, "display" is any apparatus or device capable of displaying information using, for example, a graphical user interface, etc., to perform the functionality, methods, or logic described herein such as, for example, a liquid crystal display, an organic light-emitting diode screen, a touchscreen, a cathode ray tube display, etc.

Figure 2:
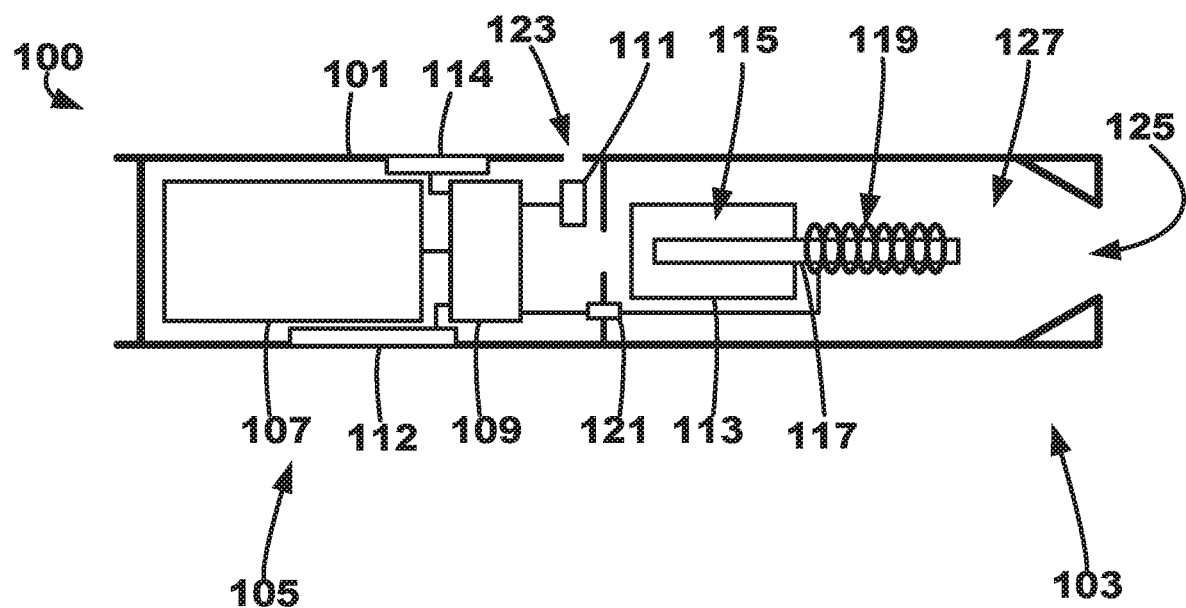
FIG. 2 is a schematic sectional view of an aerosol-generating device for controlling a production of total particulate matter (TPM) according to an example embodiment.

A flow chart of an illustrative method 10 of controlling total particulate matter production in an aerosol-generating device using an aerosol-producing substrate is depicted in FIG. 1. As shown, the method 10 may include a step 12 of providing a TPM density. The TPM density may a TPM production rate per flow rate of gas through an aerosol-generating device 100 such as shown in FIG. 2. TPM production may be represented by a mass of TPM produced per period of time such as, for example, in milligrams (mg) per second (s). The flow rate may be represented by a volume per period of time such as, for example, millilitre (ml) per second (s). Thus, in at least one aspect, TPM density may be represented by mg of TPM per second per ml per second. The TPM density may be provided by the aerosol-generating device 100, a user interface device 201, a database server 50, or input as shown and described with respect to FIG. 3.

The method 10 may further include a step 14 of determining, or measuring, a flow rate (for example, an air flow rate) through the aerosol-generating device 100 during, for example, an inhalation or puff of the aerosol-generating device 100. The flow rate may be determined using a flow sensor, such as the flow sensor 111 of the aerosol-generating device 100 described herein with respect to FIG. 2. Once the flow rate is determined in step 14, the illustrative method 10 may, pursuant to step 16, adjust the production of TPM by the aerosol-generating device 100 based on, or in response to, the determined flow rate from step 14 and a desired TPM density to target the desired TPM density. Generally, production of TPM may be increased in response to an increase in the determined flow rate, and production of TPM may be decreased in response to a decrease in the determined flow rate.

In one aspect, adjusting production of TPM by the aerosol-generating device 100 may include adjusting production of TPM to maintain the TPM density within a range around the desired TPM density such as within 20% of the desired TPM density. In further illustrative embodiments, adjusting production of TPM by the aerosol-generating device 100 may include adjusting production of TPM to maintain the TPM density within a range less than or equal to about 1% of the desired TPM density, less than or equal to about 2.5% of the desired TPM density, less than or equal to about 5% of the desired TPM density, less than or equal to about 7.5% of the desired TPM density, less than or equal to about 10% of the desired TPM density, or less than or equal to about 15% of the desired TPM density.

An illustrative aerosol-generating device 100 for controlling total particulate matter production is depicted in FIG. 2. The aerosol-generating device 100 may include a housing 101 having a mouthpiece end 103 and a body end 105. In the body end 105, there is provided an electric power supply in the form of battery 107, electric circuitry in the form of a controller 109, and a flow sensor 111. In the mouthpiece end 103, there is provided a liquid storage portion in the form of cartridge 113 containing liquid 115, a capillary wick 117, and a heater 119 comprising at least one heating element. One end of the capillary wick 117 extends into the cartridge 113 and the other end of the capillary wick 117 is surrounded by the heating element 119. The heating element 119 is connected to the electric circuitry via a connector 121. The housing 101 also includes an air inlet 123, an air outlet 125 at the mouthpiece end 103, and an aerosol-forming cavity, or chamber, 127. The connector 121 may comprise a pair of connectors configured to be removably coupled from one another. Further, the mouthpiece end 103 having the cartridge 113, the capillary wick 117, the heater 119, and one of a pair of the connectors 121 may be detachable from the housing 101.

In use, operation is as follows. Liquid 115 may be transferred or conveyed by capillary action from the cartridge 113 from the end of the wick 117 which extends into the cartridge to the other end of the wick 117 which is surrounded by the heating element 119. During a draw on the aerosol-generating device 100 at the air outlet 125, ambient air is drawn through air inlet 123. In the arrangement shown in FIG. 2, the flow sensor 111 senses an inhalation and the flow rate of the inhalation, which in turn, are used to determine the amount of power to activate the heating element 119. The battery 107 supplies energy via the controller 109 to the heating element 119 to heat the end of the wick 117 surrounded by the heating element 119. In other words, the battery 107 supplies energy under the control of the controller 109 to the heating element 119 to heat the end of the wick 117 surrounded by the heating element 119. The liquid in that end of the wick 117 is vaporized by the heating element 119 to create a vapor (e.g., supersaturated vapour). At the same time, the liquid being vaporized is replaced by further liquid moving along the wick 117 by capillary action, which may sometimes be referred to as "pumping action". The vapor (e.g., supersaturated vapour) created is mixed with and carried in the airflow from the air inlet 123 into the aerosol-forming cavity, or chamber, 127 where the vapour condenses to form an inhalable aerosol, which is carried towards the air outlet 125.

The capillary wick 117 can be made from a variety of porous or capillary materials and may have a known, predefined capillarity. Examples include ceramic- or graphite-based materials in the form of fibres or sintered powders. Wicks of different porosities can be used to accommodate different liquid physical properties such as density, viscosity, surface tension and vapour pressure. The wick 117 is suitable so that a selected amount of liquid can be delivered to the heating element 119 such that, for example, a desired amount of aerosol can be conveyed.

In another embodiment, the heating element 119 may comprise a resistive heating mesh. The resistive heating mesh may comprise a plurality of electrically conductive filaments. The electrically conductive filaments may be substantially flat. As used herein, "substantially flat" means formed in a single plane and not wrapped around or otherwise conformed to fit a curved or other non-planar shape. A flat heating mesh can be easily handled during manufacture and provides for a robust construction. Further, the electrically conductive filaments may define interstices between the filaments and the interstices may have a width of between about 10 micrometres and about 100 micrometres. The filaments give rise to capillary action in the interstices, so that in use, liquid 115 is drawn into the interstices, increasing the contact area between the heater assembly and the liquid. The wick 117 may be provided to contact the heating mesh and allow the liquid 115 to migrate to this heating mesh through the porous carrier material.

In the example embodiment shown in FIG. 2, the controller 109 is programmable. The flow sensor 111 also may be programmable. The controller 109 and flow sensor 111 can be used to manage the device operation, which may control the TPM production described herein. The controller 109 may include one or more processors and associated memory, and may further include a communication interface such as, for example, a wireless communication interface to, for example, communicate with the user interface device 201. The communication interface of the controller 109 may comprise a BLUETOOTH interface. Further, the controller 109 is programmable in order to control the supply of power to the heating element 119, which, in turn, may be used to control (for example, maintain, adjust, etc.) the TPM density of the aerosol-generating device 100.

The aerosol-generating device 100 may further include a display 112 operably coupled to the controller 109 to depict information for viewing. The display 112 may include one or more light-emitting diodes (LEDs) to indicate a selected TPM level of the aerosol-generating device 100. The LEDs may use one or more different colors, patterns, and number of LEDs lit to indicate the selected TPM level. Further, the display 112 may be a liquid crystal display (LCD) to indicate a selected TPM level of the aerosol-generating device 100.

The aerosol-generating device 100 may further include one or more buttons 114 operably coupled to the controller 109 that may be used to interoperate with the aerosol-generating device 100. In one example, the buttons 114 may be used to select, or input, the desired TPM level into the aerosol-generating device 100.

Although this illustrative aerosol-generating device 100 is a device having a liquid storage portion for a liquid substrate, it is to be understood that any aerosol-generating device configured to generate aerosol using aerosol-producing substrates may use or be used by the example embodiments described herein. Many other examples of aerosol-generating devices may be usable such as, for example, a device that uses an aerosol forming substrate that can be heated by at least one electric heating element, powered by a power supply under the control of electric circuitry. Further, for example, the device need not be a smoking device. Further, the aerosol-producing substrate may be a solid substrate, rather than a liquid substrate, and alternatively, the aerosol-producing substrate may be another form of substrate such as a gas substrate. Still further, the heating element may take any appropriate form so as to provide aerosol production or generation from the selected form or type of aerosol-producing substrate. Yet still further, the overall shape and size of the housing could be altered and the housing could comprise a separable shell and mouthpiece, and other variations are still possible.

Figure 3:
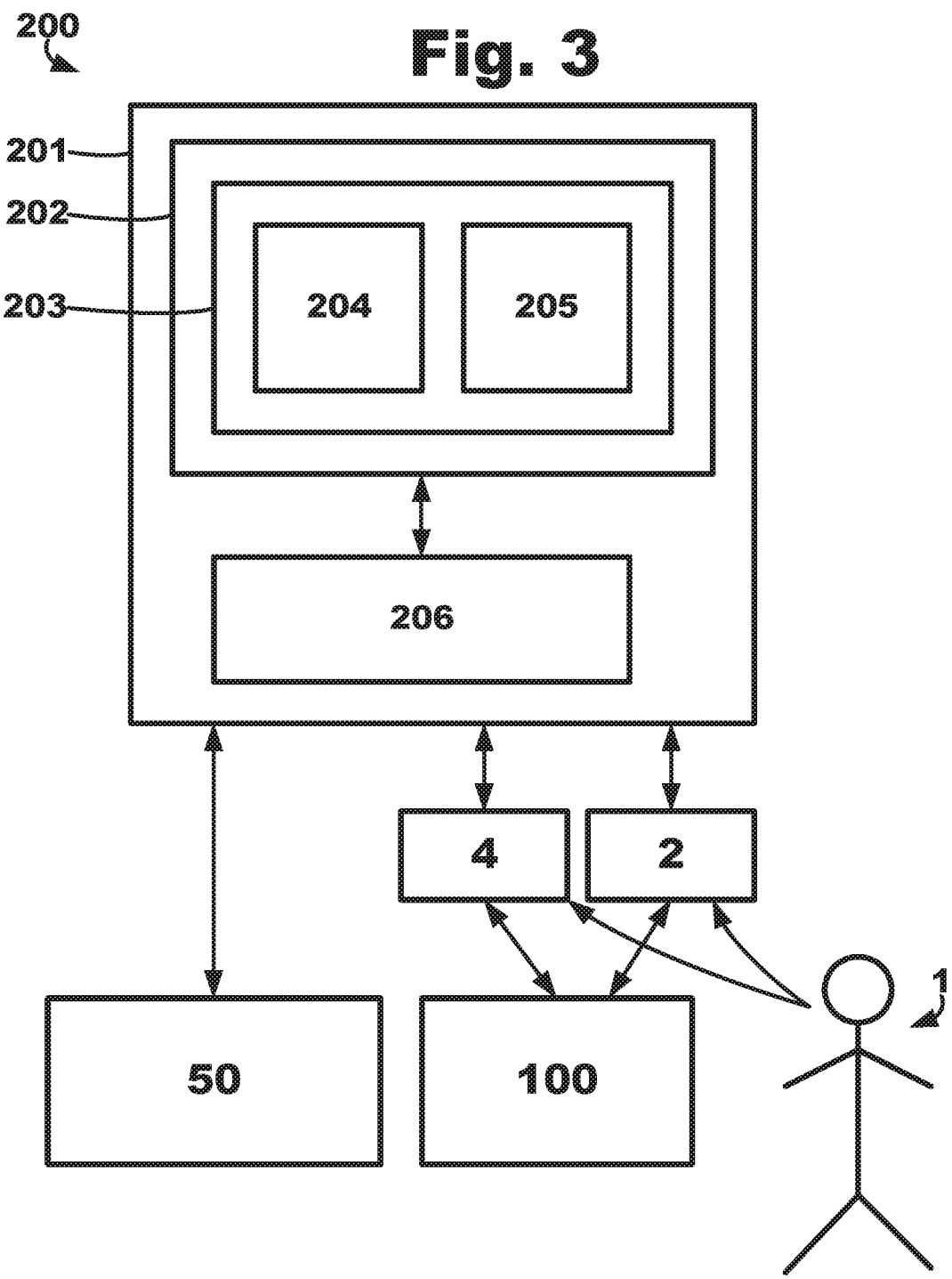
FIG. 3 is a block diagram of a system for controlling a production of total particulate matter (TPM) in an aerosol-generating device according to an example embodiment.

With reference to FIG. 3, a functional scheme of an illustrative method and an illustrative system 200 are depicted. The system 200 includes a user interface device 201 and an aerosol-generating device 100. The user interface device 201 includes a controller 202 and associated data storage 203. The data storage 203 includes programs and routines 204 such as, for example, programs and routines for the acquisition of data representative of TPM densities, air flow rates, TPM production, heater power, and any other programs or routines to execute the illustrative methods and processes described herein. The data storage 203 further includes data 205 such as the data representative of the TPM densities, air flow rates, TPM production, heater power, and the like. The user interface device 201 further includes a display 206 comprising an interactable, graphical user interface.

Block 2 represents TPM density selected, or provided, by the adult vaper 1. As shown, the selected TPM density may be provided, or input, into one or both of the user interface device 201 and the aerosol-generating device 100. Further, if the desired TPM density is selected using the aerosol-generating device 100, the desired TPM density may be provided to the user interface device 201 by the aerosol-generating device 100, and conversely, if the desired TPM density is selected using the user interface device 201, the desired TPM density may be provided to the aerosol-generating device 100 by the user interface device 201. In other words, the aerosol-generating device 100 and the user interface device 201 may synchronize, or sync, the TPM density with each other. Block 4 represents a detected type of aerosol-producing substrate that may be detected by the aerosol-generating device 100 and transmitted to the user interface device 201. Further, if the aerosol-generating device 100 is not configured to or cannot detect the type of aerosol-producing substrate, the type of aerosol-producing substrate may be input into one or more of the aerosol-generating device 100 and user interface device 201. According to this embodiment, the detected type of aerosol-producing substrate may be any type of aerosol-producing substrate such, for example, liquid aerosol-producing substrate or solid aerosol-producing substrate. The TPM density may be selected according the user interface device 201 depicted in FIG. 4. As described herein, the user interface device 201 may be a portable device that configured to establish a connection to an external database server 50, to transfer/receive data.

Figure 4:
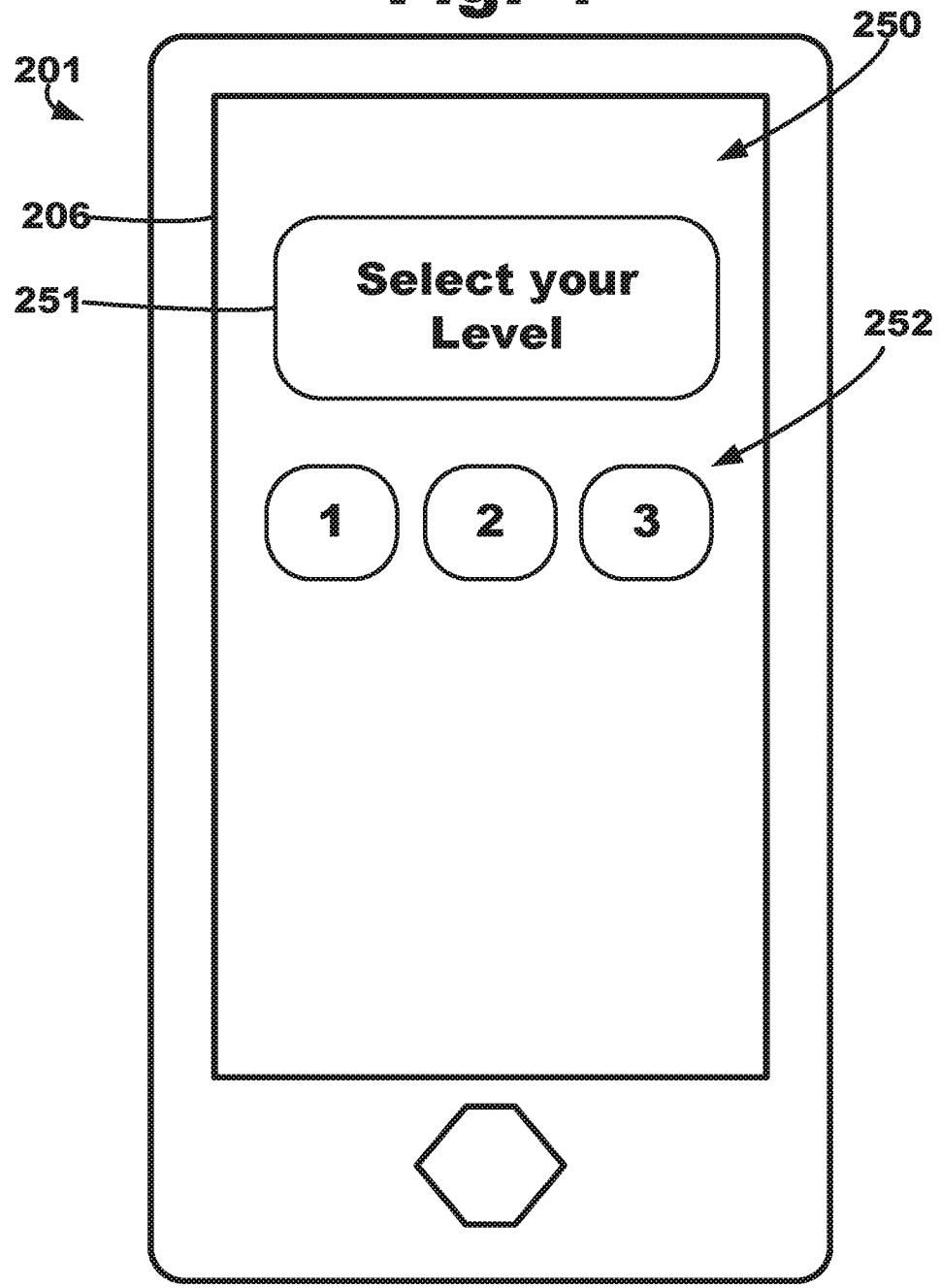
FIG. 4 is a schematic view of a graphical user interface depicting an input dialog and for use with a user interface device according to an example embodiment.

The illustrative user interface device 201 including a display 206 depicting a graphical user interface 250 is shown in FIG. 4. As depicted, the graphical user interface 250 includes a query 251 requesting a selection, or input, of a desired TPM level and a dialog 252 including selectable buttons to select, or input, the desired TPM level, that is desired. More specifically, the dialog 252 includes the following three levels: "1," "2," and "3," where "1" corresponds to a low TPM density, "3" corresponds to a high TPM density, and "2" corresponds to a TPM density between the low and high TPM densities. In other aspects, more than three or less than three TPM densities, or levels, may be used by the systems, methods, devices, and user interface devices described herein. Further, although in this example, the selectable TPM density is represented by a number, in other illustrative embodiments, the selectable TPM may be represented by the numeric value of the TPM density in milligrams (mg) per second per millilitre (ml) per second such as, for example, 0.05 [mg/s]/[/ml/s], 0.075 [mg/s]/[/ml/s], and 0.1 [mg/s]/[/ml/s].

Illustrative values of TPM density and air flow rates that affect TPM production are shown in a table of FIG. 5. In this example, the illustrative systems, devices, and methods may provide the possibility to select, or fix, a TPM density level, or power, at one of three options: 1, 2, or 3 (Low, Medium, or High). The TPM density level corresponds to a TPM density. Level 1 corresponds to a TPM density of 0.05 [mg/s]/[/ml/s], Level 2 corresponds to a TPM density of 0.075 [mg/s]/[/ml/s], and Level 3 corresponds to a TPM density of 0.1 [mg/s]/[/ml/s].

Then, when an air flow rate, or speed, is detected during an inhalation, a particular power level may be selected, or determined, based on the air flow rate and the selected TPM density. For example, if Level 2 is selected, which corresponds to a TPM density of 0.075 [mg/s]/[/ml/s], and an inhalation is at a flow rate of 30 ml/s, the illustrative systems, devices, and methods may use a power defined for 30 ml/s at TPM density level 2 to produce TPM at 2.25 mg/s to maintain or at least target the TPM density of 0.075 [mg/s]/[/ml/s]. Thus, in this example, an inhalation of over three seconds may initiate 6.75 mg of TPM production.

Further, for example, if Level 3 is selected, which corresponds to a TPM density of 0.01 [mg/s]/[/ml/s], and an inhalation is at a flow rate of 10 ml/s, the illustrative systems, devices, and methods may use a power defined for 10 ml/s at TPM density level 3 to produce TPM at 1 mg/s to maintain or at least target the TPM density of 0.1 [mg/s]/[/ml/s]. Thus, in this example, an inhalation of over three seconds may initiate 3 mg of TPM production.

Still further, for example, a configuration may occur through an app on a user interface device or the aerosol-generating device to Level 2, or Medium, which corresponds to a TPM density of 0.075 [mg/s]/[/ml/s]. When puffing is initiated, the flow rate may be measured at 10 ml/s by the flow sensor of the aerosol-generating device. Through an equation, the controller of the aerosol-generating device may adapt the power to reach the TPM density of 0.075 [mg/s]/[/ml/s]. The controller may select a power defined for 10 ml/s and 0.075 [mg/s]/[/ml/s] such that 0.75 mg of TPM may be generated per second. After a first-time period (such as, for example, one second), the puff may become stronger and increase the air flow speed to 20 ml/s, and the controller may increase immediately the power to conserve a TPM density of 0.075 [mg/s]/[/ml/s] in the aerosol.

The powers defined for each of the TPM density levels and TPM densities corresponding thereto may be depend on the type of aerosol-generating device and its aerosol-generating element or heater. In one example, the aerosol-generating element of the aerosol-generating device is operated at 6 Watts during use. Further, depending on the type of aerosol-generating device and the type of aerosol-producing substrate, the aerosol-generating element of the aerosol-generating device may be operated at about 2 Watts to about 20 Watts during use such as, for example, greater than or equal to about 3 Watts, greater than or equal to about 5 Watts, greater than or equal to about 7 Watts, greater than or equal to about 10 Watts, less than or equal to about 19 Watts, less than or equal to about 16 Watts, less than or equal to about 13 Watts, etc. Other aerosol-generating devices and the aerosol-generating elements associated therewith may be programmed into a look-up table stored in memory.

Generally, the table of FIG. 5 may provide perspective to how the illustrative systems, devices, and methods may provide the ability to fix a TPM density. As shown, the power in this example becomes just an intermediary step to provide a TPM proportional to the air flow speed detected.

In other words, the illustrative embodiments described herein may allow a pre-selection of a low, medium, or high-density aerosol delivery, and subsequently, the device may then monitor the puffs to adapt the power to the heater necessary to deliver that low, medium, or high-density aerosol based on the flow rate regime. The TPM density may be a function of the power provided to the consumable. Further, however, the relation between power and TPM density may be different as a function of the consumable design, and thus, specific equations that link power and density may be preprogrammed in the device controller.

The illustrative embodiments may further determine, or calculate, the amount of power to be delivered to the aerosol-generating element based on one or more variables or factors such as, for example, the desired TPM density and the air flow through the aerosol-generating device. In one embodiment, look-up tables correlating ranges of air flows to power to be delivered to the aerosol-generating element may be used. Such look-up tables may be stored in memory on the aerosol-generating device or the user interface device. Further, a different look-up table may be used for each desired TPM density level that is selectable. For example, one embodiment may include a look-up table for a low TPM density level, another look-up table for a medium TPM density level, and still another look-up table for a high TPM density level, each having different power values correlated to the same air flow ranges.

A look-up table depicting illustrative power values for various air flow levels usable to determine the power to generate a desired TPM density is shown in FIG. 6. This example may be a look-up table for a desired medium TPM density level. As shown, when the air flow sensed by the aerosol-generating device is between 0 ml/s and 10 ml/s, the look-up table provides a power level of 3 Watts. Further, the power is 3.5 Watts when the air flow is between 10 ml/s and 20 ml/s, 4.2 Watts when the air flow is between 20 ml/s and 30 ml/s, 5.1 Watts when the air flow is between 30 ml/s and 40 ml/s, and 6.5 Watts when the air flow is between 40 ml/s and 50 ml/s.

The air flow sensed by the aerosol-generating device and used to determine the power level for the aerosol-generating element may be monitored and used to adjust the power level as quickly as the air flow sensor may sense the air flow. In some embodiments, the power may be described as being adjusted "instantaneously" in response to air flow changes. The monitoring sampling time period may be between about 1 millisecond (ms) and about 200 milliseconds). In this way, the power level may be adjusted based on air flow between about 1000 times a second to about 5 times a second. Further, various statistical techniques and processes may be used to filter the air flow samples such as, for example, averaging a plurality of air flow samples over a given time period.

Figure 8:
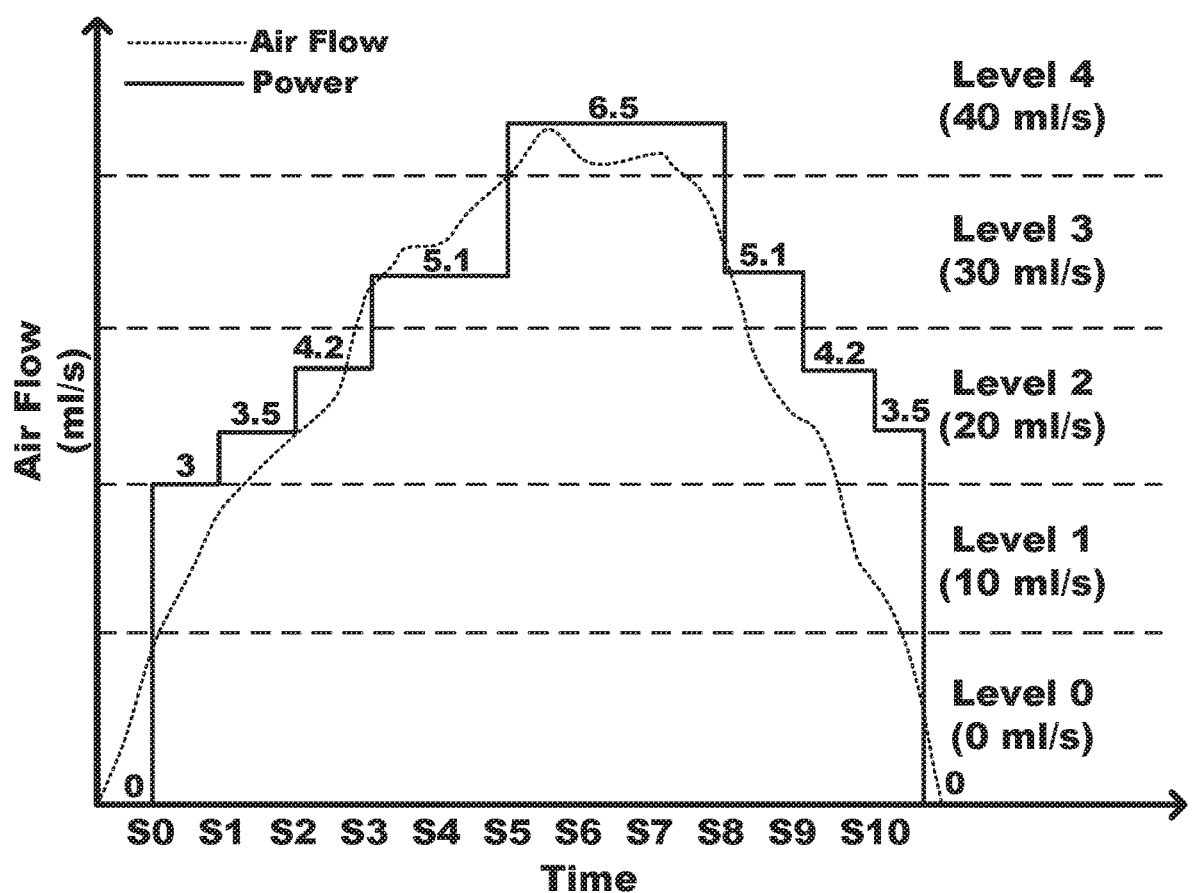
FIG. 8 is a chart of the samples depicted in the table of FIG. 7.

FIGS. 7-8 depict an inhalation in air flow and power level over time illustrating the use of various power values for various air flow levels. As shown, the air flow rate of the illustrative puff, or inhalation, starts at 0 ml/s and climbs to 41 ml/s before falling back to 0 ml/s over 10 time periods. At the outset, a puff, or inhalation, is detected when a specific air flow threshold is reached. In this example, the air flow threshold is 10 ml/s.

At each sampling point (S0, S1, S2 . . . ), the air flow is determined, and the air flow value is input into the table of FIG. 6 to determine the power level to maintain the TPM density. For example, at sample S3, the air flow measured is 33 ml/s, and 33 ml/s is within the range of 30 ml/s to 40 ml/s, which provides 5.1 Watts. Further, for example, at sample S7, the air flow measured is 41 ml/s, and 41 ml/s is within the range of 40 ml/s to 50 ml/s, which provides 6.5 Watts. Still further, for example, at sample S10, the air flow measured is 13 ml/s, and 13 ml/s is within the range of 10 ml/s to 20 ml/s, which provides 3.5 Watts.

In other words, the table of FIG. 6 may be described as allowing a power level to be determined, which may be supplied to the aerosol-generating element based on the TPM density level and the instantaneous air flow rate through the aerosol-generating device. Based on the selected TPM density level, the controller may select the suitable table that corresponds to the selected TPM density level. The TPM density level of the table of FIG. 6 is level 2, or medium level, which is then used to determine the power levels in the example shown in FIGS. 7-8.

In one embodiment, one or more transfer functions (such as polynomial calculations) relating air flow to power to be delivered to the aerosol-generating element may be used to determine, or calculate, the amount of power to be delivered to the aerosol-generating element. The transfer functions may be linear or any polynomial that may have different degrees such as, for example, a 1st degree polynomial, a 2nd degree polynomial, or a 3rd degree polynomial.

For example, a single formula, P=f(air flow rate, desired TPM density level) may be used to calculate an amount of power used to provide, or get, a desired, specific TPM density. Further, for example, one transfer function per TPM density level may be used (which, for example, may be less computationally expensive for the controller). In this way, the desired TPM density level may be selected, which will then determine the transfer function to be used. The air flow rates may be input into the transfer function to determine the amount of power to be delivered to the aerosol-generating element. As before, the air flow rate may be sampled periodically, for example, in accordance with a sampling frequency.

Figure 9:
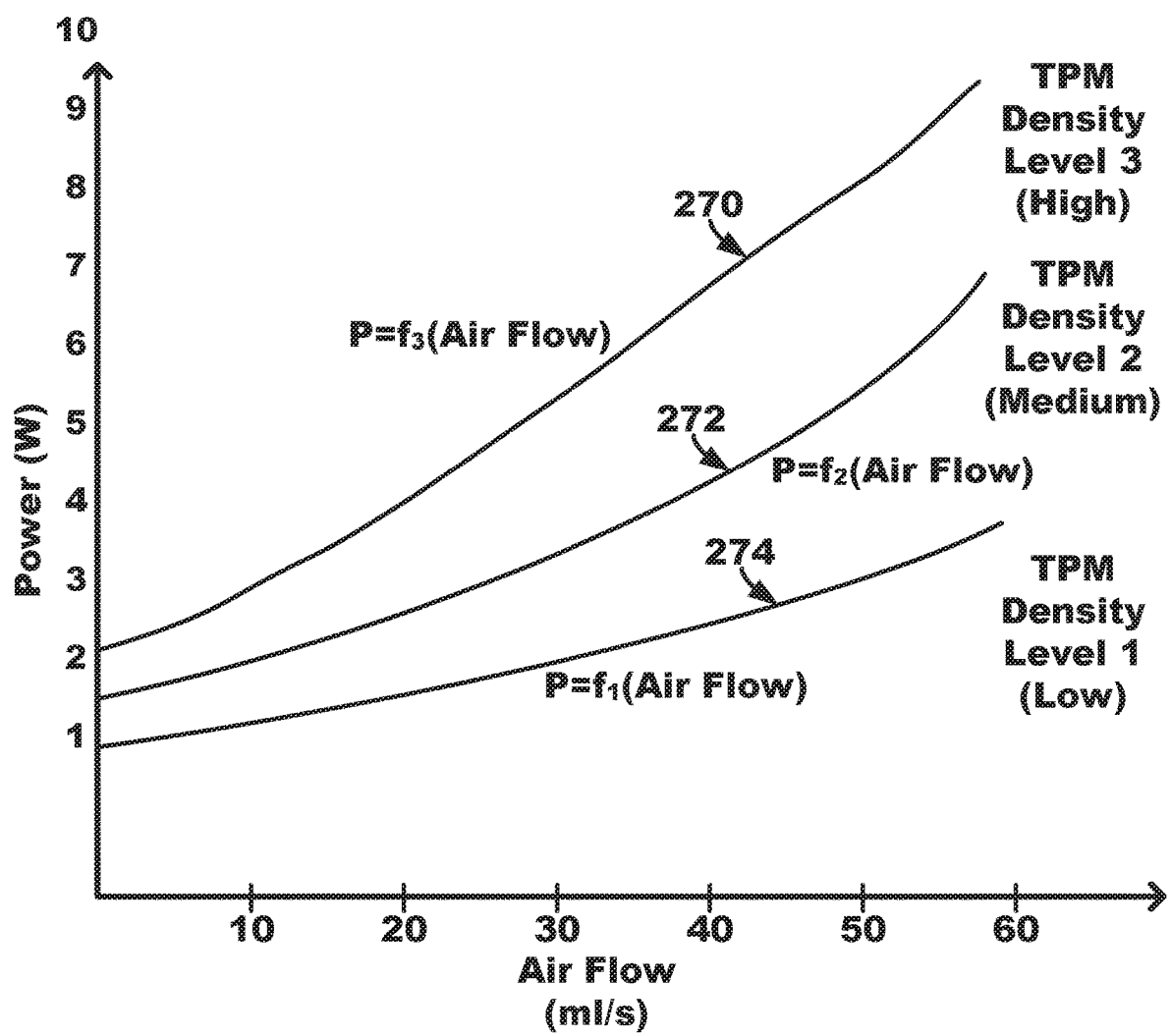
FIG. 9 is chart of power versus air flow using a transfer function according to an example embodiment.

A chart plotting three transfer functions as power versus air flow is depicted in FIG. 9. The high transfer function 270, $P=f_3$(Air Flow), corresponds to a high TPM density where more power is delivered to the aerosol-generating element than the other transfer functions. The medium transfer function 272, $P=f_2$(Air Flow), corresponds to a medium TPM density level, and the low transfer function 274, $P=f_1$(Air Flow), corresponds to a low TPM density level. Thus, the power level may be determined according the transfer function corresponding to the desired TPM density level. In other words, for each air flow sample acquired in the inhalation (S0, S1, S1 . . . ), the controller may calculate the exact power through the transfer functions.

Further, regardless of whether using the look-up table or transfer function, the sensor signal output may not be directly proportional to the air flow rate depending on the system design or system technology. Any nonlinearity shall be considered and compensated by the look-up table, transfer function, or by an extra calculation.

Figure 10:
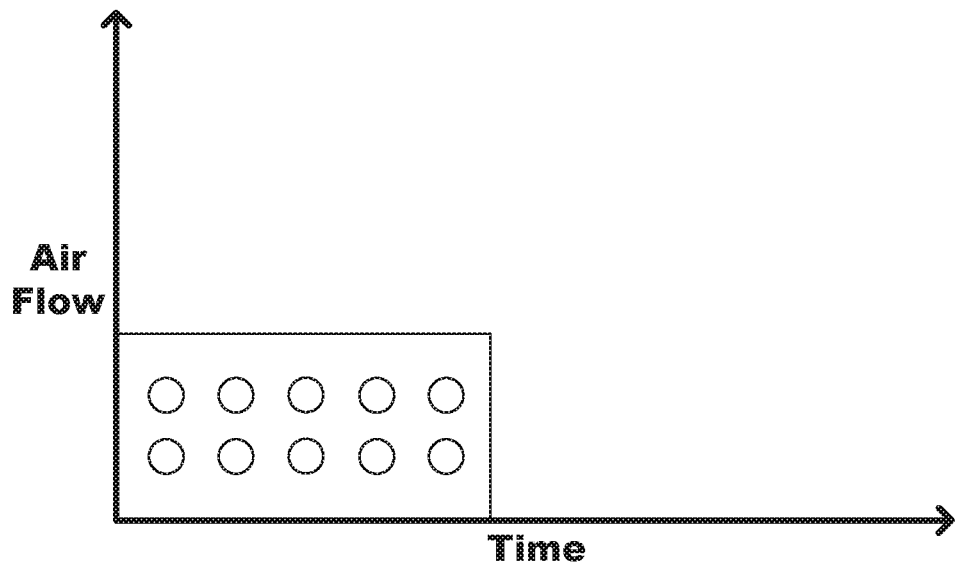
FIGS. 10-12 are charts of various scenarios depicting inhalations, or puffs, on various aerosol-generating devices according to an example embodiment.
Figure 11:
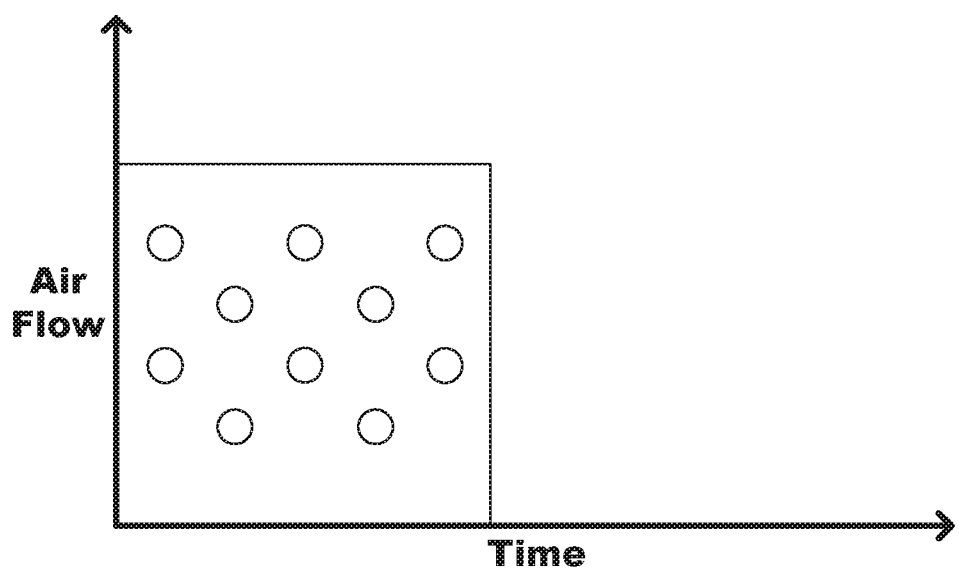
Figure 12:
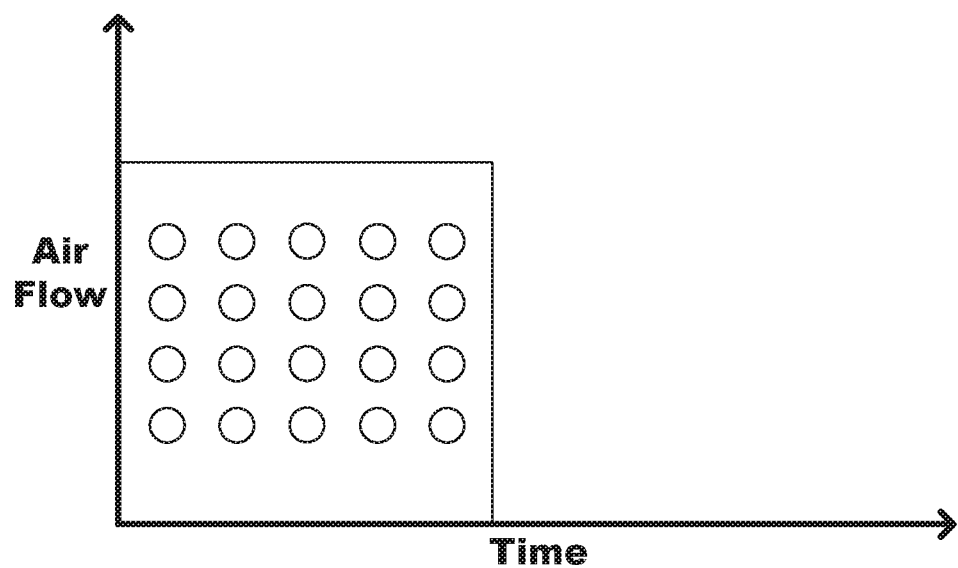

Charts depicting various scenarios depicting inhalations, or puffs, of various aerosol-generating devices are depicted in FIGS. 10-12. Aerosol-generating devices that do not adjust production of TPM in response to flow rate and a desired TPM density may deliver the similar or lesser amount of TPM over the same period of time despite stronger puffs. For example, the charts shown in FIGS. 10-11 depict an amount of TPM produced by an aerosol-generating device that does not adjust production of TPM in response to flow rate and a desired TPM density over the same period of time, such as, for example, 2 seconds. As shown, although the inhalations have the same duration, the inhalation of FIG. 11 is stronger or at a higher flow rate. However, in both puffs depicted in FIGS. 10-11, a similar amount of TPM is produced, which is represented by the circles located in the area under the curve.

Instinctively, a puff that becomes stronger may be indicative of a desire for more TPM, and in standard regulation aerosol-generating devices (such as those that do not adjust production of TPM in response to flow rate and a desired TPM density), the best-case scenario is that the TPM does not change if the puff volume is higher as shown in FIG. 11. In many scenarios, however, the TPM would even decrease if the air flow speed is increased as the heater would be cooled by the increased air flow, and thus, the only option to get more TPM would be to overextend a puff duration.

By adapting the power to conserve a specific TPM density, TPM production would increase with the air speed, or flow rate, as illustrated in FIG. 12. As shown, the air flow speed is the same as shown in FIG. 11 and for the same duration as shown in both FIGS. 10-11. However, in this example, the amount of TPM production has increased to, for example, double that of FIGS. 10-11. By keeping a specific TPM density, a repeatable, suitable TPM may be obtained in reasonable puff durations. Furthermore, it is possible to instinctively adapt the air speed as a function of the desired TPM without requiring an overextended or prolonged puff duration.

Thus, systems, devices, and methods for controlling TPM production using aerosol-producing substrates are described. Various modifications and variations will be apparent to those skilled in the art without departing from the scope and spirit of the teachings herein. Although the claimed invention has been described in connection with various example embodiments, it should be understood that the invention as claimed should not be unduly limited to such embodiments. Indeed, various modifications of the described modes which are apparent to those ordinarily skilled in the electrical arts, computer arts, and aerosol-generating device manufacturing or related fields are intended to be within the scope of the following claims.

The invention claimed is:

1. A method of controlling a production of a total particulate matter (TPM) in an aerosol-generating device, the method comprising:
   determining a flow rate of a gas through the aerosol-generating device; and
   adjusting the production of the total particulate matter (TPM) by the aerosol-generating device in response to the flow rate and a target TPM density, the target TPM density being a target TPM production rate per flow rate of the gas through the aerosol-generating device, the adjusting including determining and modifying an amount of power to be used by the aerosol-generating device as a function of at least the flow rate, modifying the amount of power includes modifying the amount of power to be in a first range in response to the flow rate being greater than or equal to a first flow threshold, modifying the amount of power to be in a second range in response to the flow rate being greater than or equal to a second flow threshold, and modifying the amount of power to be in a third range in response to the flow rate being greater than or equal to a third flow threshold.

2. The method of claim 1, further comprising:
   selecting the target TPM density prior to the determining of the flow rate and the adjusting of the production.

3. The method of claim 1, wherein the adjusting includes increasing the production of the TPM in response to an increase in the flow rate and decreasing the production of the TPM in response to a decrease in the flow rate.

4. The method of claim 1, wherein the adjusting is performed to maintain a produced TPM density within a range of the target TPM density.

5. The method of claim 4, wherein the range is within 20% of the target TPM density.

6. The method of claim 1, wherein the adjusting is further in response to a type of an aerosol-producing substrate used by the aerosol-generating device.

7. The method of claim 1, wherein the adjusting is further based on the target TPM density being associated with a type of an aerosol-producing substrate for the aerosol-generating device.

8. The method of claim 1, further comprising:
   selecting one of a plurality of different TPM densities as the target TPM density.

9. The method of claim 1, wherein the production of the TPM involves an aerosol-producing substrate including a nicotine-containing material.

10. An aerosol-generating device comprising:
    an aerosol-generating element configured to heat an aerosol-producing substrate for a production of a total particulate matter (TPM);
    a flow sensor configured to measure a flow rate of a gas to the aerosol-generating element;
    a power source configured to provide power to the aerosol-generating element; and
    a controller including one or more processors and operably coupled to the power source, the flow sensor, and the aerosol-generating element, the controller configured to adjust the production of the TPM by determining an amount of power to be used by the aerosol-generating device in response to the flow rate and a target TPM density such that the power is in the first range in response to the flow rate being greater than or equal to a first flow threshold, the power is in a second range in response to the flow rate being greater than or equal to a second flow threshold, and the power is in a third range in response to the flow rate being greater than or equal to a third flow threshold, the target TPM density being a target TPM production rate per flow rate of the gas.

11. A non-transitory computer readable storage medium including a computer program stored thereon which, when run on programmable electric circuitry, causes the programmable electric circuitry to determine a flow rate of a gas through an aerosol-generating device and to adjust a production of a total particulate matter (TPM) by determining an amount of power to be used by the aerosol-generating device in response to the flow rate and a target TPM density, the amount of power being a function of at least the flow rate such that the power is in a first range in response to the flow rate being greater than or equal to a first flow threshold, the power is in a second range in response to the flow rate being greater than or equal to a second flow threshold, and the power is in a third range in response to the flow rate being greater than or equal to a third flow threshold, the target TPM density being a target TPM production rate per flow rate of the gas through the aerosol-generating device.

* * * * *